US006559330B1

(12) United States Patent
Platzek et al.

(10) Patent No.: US 6,559,330 B1
(45) Date of Patent: May 6, 2003

(54) CALCIUM COMPLEX OF [[(4R)-4-[BIS{CARBOXY-.KAPPA.O)METHYL] AMINO-.KAPPA.N]-6,9-BIS [(CARBOXY.KAPPA.O)METHYL]-1-[(4,4-DIPHENYLCYCLOHEXYL)OXY]-1-HYDROXY-2-OXA-6,9-DIAZA-1-PHOSPHAUNDECAN-11-YLIC-ACID-.KAPPA.N6,.KAPPA.N9,.KAPPA.011]1-OXIDATO(6-)]-, HEXAHYDROGEN, ITS SALTS, PHARMACEUTICAL AGENTS THAT CONTAIN THESE COMPLEXES, THEIR USE IN TREATMENT AND AS ADDITIVES IN DIAGNOSIS, AS WELL AS PROCESSES FOR THE PRODUCTION OF THE COMPLEXES AND AGENTS

(75) Inventors: Johannes Platzek, Berlin (DE); Ulrich Niedballa, Berlin (DE); Guenter Michl, Ruedersdorf (DE)

(73) Assignee: Schering Aktiengesellschaft (DE)

( * ) Notice: Subject to any disclaimer, the term of this patent is extended or adjusted under 35 U.S.C. 154(b) by 0 days.

(21) Appl. No.: 09/659,554

(22) Filed: Sep. 11, 2000

Related U.S. Application Data

(60) Provisional application No. 60/266,324, filed on Sep. 15, 1999.

(30) Foreign Application Priority Data

Sep. 9, 1999 (DE) .......................... 199 44 893

(51) Int. Cl.[7] .......................... C07F 9/02; A01N 57/00; A61K 31/555; A61B 5/055
(52) U.S. Cl. ...................... 558/169; 514/114; 514/184; 424/9.3; 424/9.35
(58) Field of Search ................................ 424/9.35, 9.3; 514/184, 114; 558/169

(56) References Cited

U.S. PATENT DOCUMENTS

| 4,647,447 | A | | 3/1987 | Gries et al. | |
|---|---|---|---|---|---|
| 5,082,649 | A | | 1/1992 | VanDeripe | |
| 5,098,692 | A | | 3/1992 | Gries et al. | |
| 5,648,063 | A | | 7/1997 | Gries et al. | |
| 5,919,967 | A | * | 7/1999 | Amedio et al. | .......... 536/25.34 |

FOREIGN PATENT DOCUMENTS

| EP | 071564 | 2/1983 |
|---|---|---|
| EP | 0 454 078 A2 | 10/1991 |
| WO | 9623526 | 8/1969 |

OTHER PUBLICATIONS

European Patent Office, International Search from PCT/EP00/08694, dated Dec. 4, 2000.*

Aime, S et al: "Contrast Agent for magnetic resonance angiographic applications" JBIC vol. 4, No. 6, 1999 pp. 766–774.

* cited by examiner

*Primary Examiner*—Sreeni Padmanabhan
*Assistant Examiner*—Michael A. Willis
(74) *Attorney, Agent, or Firm*—Millen, White, Zelano & Branigan, P.C.

(57) ABSTRACT

The invention relates to the calcium complex of [[(4R)-4-[bis[(carboxy-.kappa.O)methyl]amino-.kappa.N]-6,9-bis [(carboxy-.kappa.O)methyl]-1-[(4,4-diphenylcyclohexyl) oxy]-1-hydroxy-2-oxa-6,9-diaza-1-phosphaundecan-11-ylic-acid-.kappa.N6,.kappa. N9,.kappa.011]1-oxidato(6-)]-, tetrahydrogen(MS-325) and its salts, pharmaceutical agents that contain these complexes, for the production of agents for the reduction of effects that are caused by heavy metals as well as processes for their production.

1 Claim, 2 Drawing Sheets

CALCIUM COMPLEX OF [[(4R)-4-[BIS{CARBOXY-.KAPPA.O)METHYL] AMINO-.KAPPA.N]-6,9-BIS [(CARBOXY.KAPPA.O)METHYL]-1-[(4,4-DIPHENYLCYCLOHEXYL)OXY]-1-HYDROXY-2-OXA-6,9-DIAZA-1-PHOSPHAUNDECAN-11-YLIC-ACID-.KAPPA.N6,.KAPPA.N9,.KAPPA.011]1-OXIDATO(6-)]-, HEXAHYDROGEN, ITS SALTS, PHARMACEUTICAL AGENTS THAT CONTAIN THESE COMPLEXES, THEIR USE IN TREATMENT AND AS ADDITIVES IN DIAGNOSIS, AS WELL AS PROCESSES FOR THE PRODUCTION OF THE COMPLEXES AND AGENTS

This application claims priority of U.S. provisional application Serial No. 60/266,324, filed Sep. 15, 1999.

The invention relates to the subject that is characterized in the claims, i.e., the calcium complex of [[(4R)-4-[bis [(carboxy-.kappa.O)methyl]amino-.kappa.N]-6,9-bis [(carboxy.kappa.O)methyl]-1-[(4,4-diphenylcyclohexyl) oxy]-1-hydroxy-2-oxa-6,9-diaza-1-phosphaundecan-11-ylic-acid-.kappa.N6,.kappa.N9,.kappa.011]1 oxidato(6-)]-, hexahydrogen, its salts, pharmaceutical agents that contain these complexes, for the production of agents for reducing effects that are caused by heavy metals as well as processes for their production.

In medicine, complex compounds are used in particular for the treatment of heavy metal poisonings, pathological surfeit of iron as well as for the production of pharmaceutical agents for the imaging diagnosis.

EP 71564 describes, i.a., the meglumine salt of the gadolinium(III) complex of diethylenetriaminepentaacetic acid (DTPA) as a contrast medium for NMR tomography. A preparation that contains this complex was approved worldwide as the first NMR contrast medium under the name Magnevist®. This contrast medium is dispersed extracellularly after intravenous administration and is eliminated renally by glomerular secretion. A passage of intact cell membranes is virtually not observed. Magnevist® is especially well-suited for the visualization of pathological areas (e.g., inflammations, tumors).

DTPA- or Ca-DTPA-containing compounds are further used clinically in the case of metal poisonings.

Therefore, there is a need for agents to reduce effects that are caused by heavy metals.

The object of the invention is to make available such compounds and agents as well as to provide a process for their production. The achievement of this object is carried out by this invention.

Laid-open specification WO 96/23526 describes the use of gadolinato(3-),[[(4R)-4[bis[(carboxy-.kappa.O)methyl] amino-.kappa.N]-6,9-bis[(carboxy-.kappa.O)methyl]-1-[(4, 4-diphenylcyclohexyl)oxy]-1-hydroxy-2-oxa-6,9-diaza-1-phosphaundecan-11-ylic-acid-.kappa.N6,.kappa.N9, kappa.011]1-oxidato(6-)]-trihydrogen, also referred to as Gd-MS-325, as a blood pool agent. Gd-MS-325 is distinguished in that it binds to human serum albumin (HSA) and thus is retained in the intravascular space. The production of a Gd-MS-325 formulation is also described in WO 96/23526. Thus, in Example 10, the production of a 200 mmol solution of Gd-MS-325 (meglumine salt) with a 5% excess complexing agent MS-325 is described. The addition of calcium salts to the formulation is claimed in claim 101, but it is not specifically disclosed in the text and in the examples.

WO-96/23526 describes the production of a Gd-MS-325 formulation with 5% excess complexing agent MS-325 (Example 10). The attempt to produce the Ca-MS-325 complex in this formulation was unsuccessful (see Tests I–III).

An attempt was made to complex the 5% excess complexing agent with Ca-hydroxide or Ca-carbonate in situ. In this case, cloudiness occurred, especially in the case of large batches (1–10 l). An AAS analysis of this cloudy material yielded that in this connection, this is a Gd-containing component. (During the complexing process, MS-325 probably forms a kinetically preferred intermediate product, which results in cloudiness because of its poor solubility. They are presumably Ca complexes of phosphate ester. The fact that it is a kinetically-produced intermediate product is confirmed in that if such a cloudy solution is refluxed for 48 hours, the precipitate dissolves, and a clear solution is produced.) In addition, using HPLC, partial decomposition is already observed. Because of the cloudiness that is to be filtered off, whose intensity partially depends on how quickly the calcium is added to the solution, no reproducible contents of Ca-MS-325 and Gd-MS-325 are obtained in the formulation. This procedure for the galenical production of such pharmaceutical formulations is thus ultimately not acceptable.

The object was therefore also to make available a formulation of Gd-MS-325 that corresponds to the galenical requirements, i.e., among other things is not cloudy. This object is achieved by this invention.

It has been found that the above-mentioned object is achieved by the separate production of the Ca complex of the MS-325 ligand essentially free of MS-325 chelates of metals having use in diagnostic imaging, e.g., paramagnetic metals and those suitable for x-ray or ultrasound imaging, i.e., of atomic numbers 21–29, 42, 44, 57–83, and of radioactive metals, e.g., Tc, Re, Co, Cu, Au, Ag, Pb, Bi, In, Ga, or in general for ultraviolet/visible/infrared imaging, any metal chelate, (collectively termed "imaging metals"). (See WO 96/23,526). Then there occurs subsequent addition to the, e.g., Gd-MS-325 solution. This is shown, e.g., in examples 14–29 wherein in each case the solution produced is clear and not cloudy.

Formulations that are produced in this way also show constant and reproducible analytical data in the case of large batches. In addition, they have a better compatibility, more complete metal excretion and better cardiovascular system properties than the original Gd-MS-325 formulation.

The invention therefore relates to the calcium complex of [[(4R)-4-[bis[(carboxy.kappa.O)methyl]amino-.kappa.N]-6, 9-bis[(carboxy-.kappa.O)methyl]-1-[(4,4-diphenylcyclohexyl)oxy]-1-hydroxy-2-oxa-6,9-diaza-1-phosphaundecan-11-ylic-acid-.kappa.N6,.kappa.N9, .kappa.011]1-oxidato(6-)]-, hexahydrogen, its production and the salts of these complexes with physiologically compatible inorganic and/or organic cations, such as, e.g., sodium, calcium, potassium, meglumine, ethanolamine, diethanolamine, morpholine, glucamine, dimethylglucamine, lysine, arginine and/or ornithine, and the galenical formulations with Gd-MS-325 that are thus produced.

The invention further relates to the use of Ca-MS-325 and its salts for the production of pharmaceutical agents, especially as an antidote against heavy metal poisonings.

Production of the Compounds According to the Invention

The complexing agent is converted into the calcium complex (Ca-MS-325) by reaction with calcium hydroxide solution, calcium oxide, calcium carbonate or calcium bicarbonate. Then, if desired, existing acid hydrogen atoms of acid groups are substituted by cations of inorganic and/or organic bases or amino acids.

In this case, the neutralization takes place with the help of inorganic bases (e.g., hydroxides, carbonates or bicarbonates) of, e.g., sodium, potassium, lithium or calcium and/or organic bases, such as, i.a., primary, secondary and tertiary amines, such as, e.g., ethanolamine, glucamine, N-methyl- and N,N-dimethylglucamine as well as basic amino acids, such as, e.g., lysine, arginine and ornithine.

Since the Ca complex contains four free acid groups, it may be advisable to produce neutral mixed salts, which contain both inorganic and organic cations as counterions.

This can happen, for example, by Ca-MS-325 being reacted in aqueous solution with the oxide or salt of the desired metal and optionally the amount of an inorganic or organic base that is required for neutralization, the complex salt that is formed being isolated and optionally purified. The sequence of the addition of base can be arbitrary.

The production of the Gd-MS-325 formulations according to the invention takes place by the calcium complex compounds according to the invention together with Gd-MS-325—optionally by adding the additives that are commonly used in galenicals—being dissolved in aqueous medium and then the solution optionally being sterilized. It can also be advantageous to produce the latter by the calcium complex compounds according to the invention being reacted with free complexing agent MS-325 and the stoichiometric amount of gadolinium oxide or salt as well as the amount of an inorganic or organic base in aqueous medium that is required for neutralization of the gadolinium complex. Suitable additives are, for example, physiologically harmless buffers (such as, for example, tromethamine), electrolytes (such as, for example, sodium chloride) as well as antioxidants (such as, for example, ascorbic acid).

The pharmaceutical agents according to the invention contain 1 $\mu$mol/l–1 mol/l of the Gd complex salt, preferably 0.5 mmol/l–500 mmol/l and 0.05–15 mol %, preferably 0.5–5 mol %, of Ca-MS-325 and are generally dosed in amounts of 0.005–2 mmol/kg of body weight, preferably 50 $\mu$mol/kg–500 $\mu$mol/kg.

The following examples are used for a more detailed explanation of the subject of the invention.

Test of the In-situ Production of Gd-MS-325 with 5 Mol % of Ca-MS-325

I
Production of an In-situ Formulation of the Gadolinium Complex of MS-325 as Meglumine Salt (200 mmol) with 5% Ca-MS-325 Excess Complexing Agent 181.25 g (0.5 mol) of gadolinium oxide, 815.35 g (1.05 mol/95% content (according to weight) of MS-325 (ligand) and 683.25 g (3.5 mol) of N-methylglucamine are added to 3500 ml of deionized water, and then 3.70 g (50 mmol) of calcium hydroxide is added. It is stirred for 6 hours at 95° C. A cloudy solution is formed. After cooling, the solution is made up with deionized water to a volume of 5000 ml and then filtered off from the cloudy material (2 $\mu$ filter).

The cloudiness precipitate is dried in a vacuum (60° C.) (yield: 2.86 g) and dissolved in nitric acid/hydrogen peroxide (microwave) for AAS analysis. A Gd content of 8.1% (relative to the solid) was found.

II
Production of an In-situ Formulation of the Gadolinium Complex of MS-325 as Meglumine Salt (200 mmol) with 5% Ca-MS 325 Excess Complexing Agent).

181.25 g (0.5 mol) of gadolinium oxide, 815.35 g (1.05 mol/about 95% content) (according to weight) of MS-325 (ligand) and 683.25 g (3.5 mol) of N-methylglucamine are added to 3500 ml of deionized water, and then 5.00 g (50 mmol) of calcium carbonate is added. It is stirred for 6 hours at 95° C. A cloudy, opaque solution is formed. After cooling, it is made up with deionized water to a total volume of 5000 ml, and then it is filtered off from the cloudy material (2 $\mu$ filter). The cloudiness precipitate that is filtered off is dried (60° C. in a vacuum), yield: 3.14 g . (For AAS analysis, it is dissolved in nitric acid/hydrogen peroxide (microwave)). A Gd content of 9.6% (relative to the solid) was found.

III
Production of an In-situ Formulation of the Gadolinium Complex of MS-325 as Meglumine Salt (200 mmol) with 5% Ca-MS 325 Excess Complexing Agent).

18.12 g (50 mmol) of gadolinium oxide, 81.54 g (105 mol/about 95% content (according to weight) of MS-325 ligand and 68.3 g (350 mmol) of N-methylglucamine are added to 350 ml of deionized water, and then 0.37 g (5 mmol) of calcium hydroxide is added. It is refluxed for 48 hours (in this case, the initially cloudy colorless solution slowly clears up/color light yellow), it is allowed to cool and made up with deionized water to a total volume of 500 ml. The light yellow solution is filtered and analyzed by HPLC. The content of Gd-MS-325 was determined with the 100% method (external standard: HPLC-purified Gd-MS 325). A content of 96.3% was produced. The low content and the yellow coloration indicate decomposition.

For comparison: Content after HPLC/95° C. (6 hours): 98.9%.

EXAMPLES ACCORDING TO THE INVENTION

EXAMPLE 1

Figure 1:
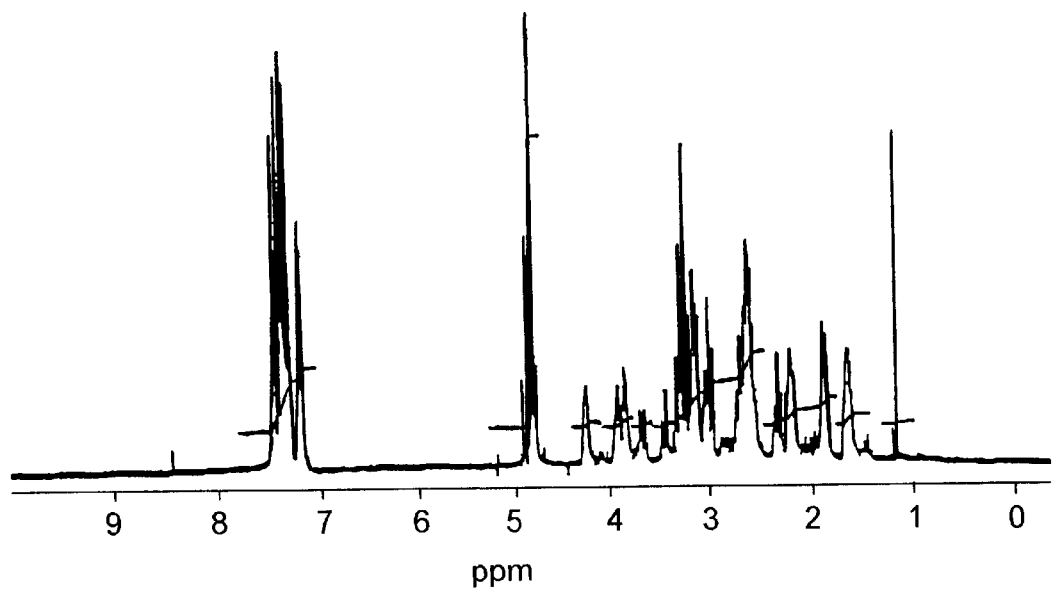
FIG. 1 is $^1$H-NMR of Example 1.
Figure 2:
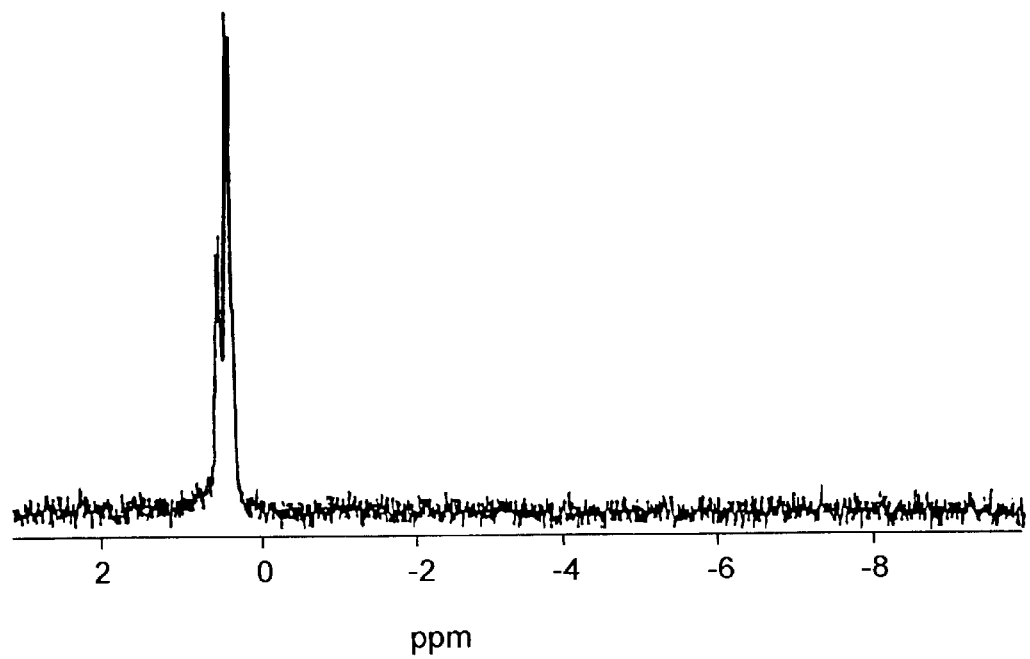
FIG. 2 is $^{31}$P-NMR of Example 1.
Figure 3:
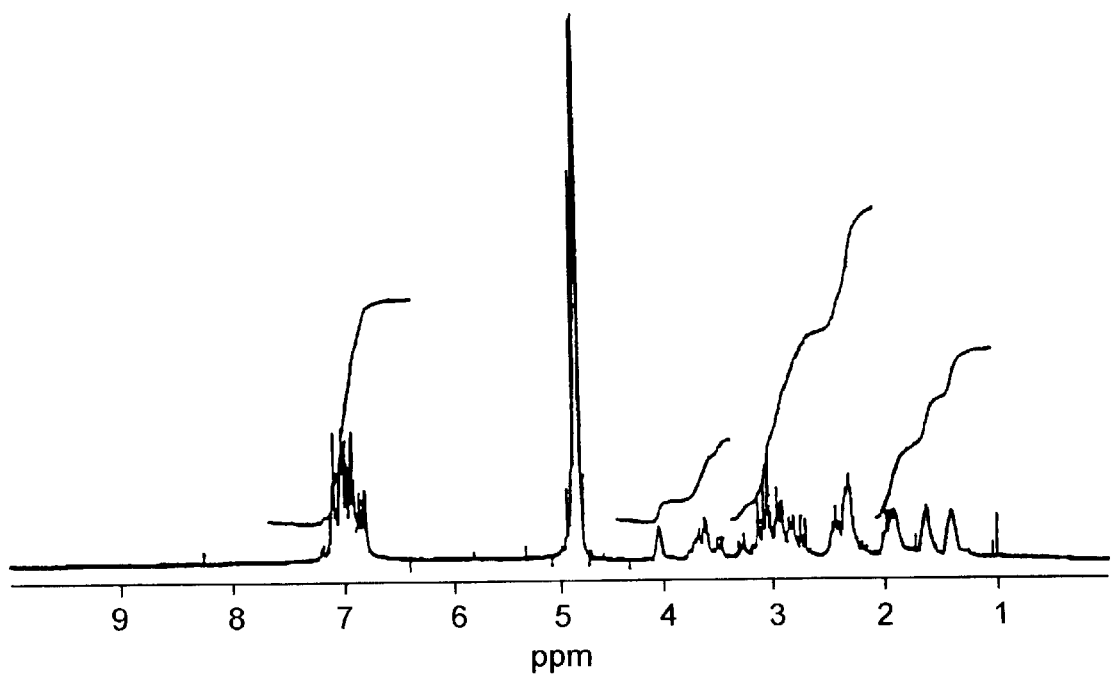
FIG. 3 is $^1$H-NMR of Example 2.
Figure 4:
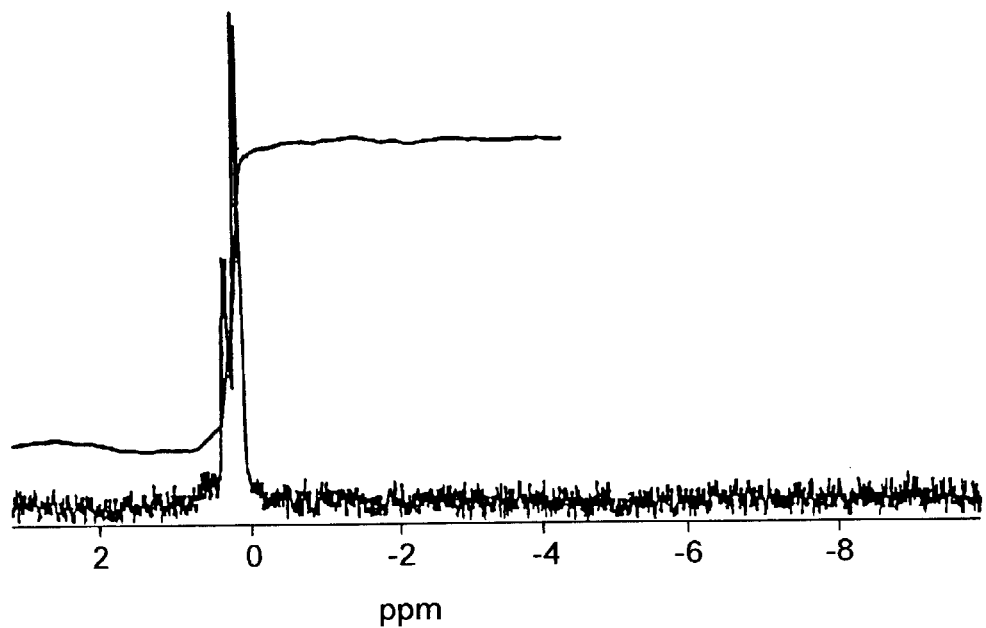
FIG. 4 is $^{31}$P-NMR of Example 2.

Calcium(4-),[[(4R)-4-[bis[(carboxy-.kappa.O)methyl]amino-.kappa.N]-6,9-bis[(carboxy-.kappa.O)methyl]-1-[(4,4-diphenylcyclohexyl)oxy]-1-hydroxy-2-oxa-6,9-diaza-1-phosphaundecan-11-ylic-acid-.kappa.N6,.kappa.N9,.kappa.011]1-oxidato(6-)]-, Tetrasodium 10.0 g (12.88 mmol/95% content (according to weight)) of MS-325 ligand, 0.954 g (12.88 mmol) of calcium hydroxide and 1.546 g (38.64 mmol) of sodium hydroxide are dissolved in 2000 ml of deionized water and stirred for 5 hours at 95° C. It is allowed to cool, and another 0.515 g (12.88 mmol) of sodium hydroxide is added, filtered with a 2 $\mu$ filter, and the title product is isolated from the filtrate by freeze-drying as a colorless, amorphous powder.

Yield: 12.40 g (quantitative) of water content: 10.3%; Elementary analysis (relative to anhydrous substance): Cld: C, 45.89/H, 4.43/N, 4.87/Ca, 4.64/Na, 10.65/P, 3.59. Fnd: C, 46.01/H, 4.52/N, 4.99/Ca, 4.53/Na, 10.77/P, 3.70.

EXAMPLE 2

Calcium(4-),[[(4R)-4-[bis[(carboxy-.kappa.O)methyl]amino-.kappa.N]-6,9-bis[(carboxy-.kappa.O)methyl]-1-[(4,4-diphenylcyclohexyl)oxy]-1-hydroxy-2-oxa-6,9-diaza-1-phosphaundecan-11-ylic-acid-.kappa.N6,.kappa.N9,.kappa.011]1-oxidato(6-)]-, Calcium, Disodium 10.0 g (12.88 mmol/95% content (according to weight)) of MS-325 ligand, 2.578 g (25.76 mmol) of calcium carbonate and 0.515 g (12.88 mmol) of sodium hydroxide are dissolved in 2000 ml of deionized water and stirred for 5 hours at 95° C. It is allowed to cool, and another 0.515 g (12.88 mmol) of sodium hydroxide is added, filtered with a 2 $\mu$ filter, and the title product is isolated from the filtrate by freeze-drying as a colorless, amorphous powder.

Yield: 12.25 g (quantitative), water content: 9.8%; Elementary analysis (relative to anhydrous substance): Cld: C, 46.21/H, 4.47/N, 4.90/Ca, 9.34/Na, 5.36/P, 3.61. Fnd: C, 46.32/H, 4.55/N, 5.00/Ca, 9.22/Na, 5.45/P, 3.73.

EXAMPLE 3

Calcium(4-),[[(4R)-4-[bis[(carboxy-.kappa.O) methyl]amino-.kappa.N]-6,9-bis[(carboxy-.kappa.O) methyl]-1-[(4,4-diphenylcyclohexyl)oxy]-1-hydroxy-2-oxa-6,9-diaza-1-phosphaundecan-11-ylic-acid-.kappa.N6,.kappa.N9,.kappa.011]1-oxidato (6-)]-, Dicalcium 10.0 g (12.88 mmol/95% content (according to weight)) of MS-325 ligand, 3.867 g (38.64 mmol) of calcium carbonate are dissolved in 200 ml of deionized water and stirred for 5 hours at 95° C. It is allowed to cool, filtered with a 2 $\mu$ filter, and the title product is isolated from the filtrate by freeze-drying as a colorless, amorphous powder.

Yield: 11.91 g (quantitative), water content: 7.9%; Elementary analysis (relative to anhydrous substance): Cld: C, 46.53/H, 4.50/N, 4.93/Ca, 14.11/P, 3.64. Fnd: C, 46.41/H, 4.61/N, 5.02/Ca, 14.22/P, 3.75.

EXAMPLE 4

Calcium(4-),[[(4R)-4-[bis[(carboxy-.kappa.O) methyl]amino-.kappa.N]-6,9-bis[(carboxy-.kappa.O) methyl]-1-[(4,4-diphenylcyclohexyl)oxy]-1-hydroxy-2-oxa-6,9-diaza-1-phosphaundecan-11-ylic-acid-.kappa.N6,.kappa.N9,.kappa.011]1-oxidato (6-)]-, Tetrameglumine 10.0 9 (12.88 mmol/95% content (according to weight)) of MS-325 ligand, 1.288 g (12.88 mmol) of calcium carbonate and 8.80 g (45.08 mmol) of meglumine are dissolved in 2000 ml of deionized water and stirred for 5 hours at 95° C. It is allowed to cool, and another 1.257 g (6.44 mmol) of meglumine is added, filtered with a 2 $\mu$ filter, and the title product is isolated from the filtrate by freeze-drying as a colorless, amorphous powder.

Yield: 22.27 g (quantitative), water content: 10.0%; Elementary analysis (relative to anhydrous substance): Cld: C, 47.07/H, 7.12/N, 6.30/Ca, 2.57/P, 1.99. Fnd: C, 47.20/H, 7.21/N, 6.43/Ca, 2.69/P 2.10.

EXAMPLE 5

Calcium(4-),[[(4R)-4-[bis[(carboxy-.kappa.O) methyl]amino-.kappa.N]-6,9-bis[(carboxy-.kappa.O) methyl]-1-[(4,4-diphenylcyclohexyl)oxy]-1-hydroxy-2-oxa-6,9-diaza-1-phosphaundecan-11-ylic-acid-.kappa.N6,.kappa.N9,.kappa.011]1-oxidato (6-)]-, Calcium, Dimeglumine 10.0 g (12.88 mmol/95% content (according to weight)) of MS-325 ligand, 1.91 g (25.76 mmol) of calcium hydroxide and 3.77 g (19.32 mmol) of meglumine are dissolved in 200 ml of deionized water and stirred for 5 hours at 95° C. It is allowed to cool, and another 1.257 g (6.44 mmol) of meglumine is added, filtered with a 2 $\mu$ filter, and the title product is isolated from the filtrate by freeze-drying as a colorless, amorphous powder.

Yield: 17.06 g (quantitative), water content: 9.1%; Elementary analysis (relative to anhydrous substance): Cld: C, 46.88/H, 6.19/N, 5.82/Ca, 6.66/P 2.57. Fnd: C, 47.01/H, 6.29/N, 5.93/Ca, 6.58/P, 2.69.

EXAMPLE 6

Calcium(4-),[[(4R)-4-[bis[(carboxy-.kappa.O) methyl]amino-.kappa.N]-6,9-bis[(carboxy-.kappa.O) methyl]-1-[(4,4-diphenylcyclohexyl)oxy]-1-hydroxy-2-oxa-6,9-diaza-1-phosphaundecan-11-ylic-acid-.kappa.N6,.kappa.N9,.kappa.011]1-oxidato (6-)]-, Calcium, Dihydrogen 10.0 g (12.88 mmol) of 95% content (according to weight) of MS-325 ligand and 1.91 g (25.76 mmol) of calcium hydroxide are dissolved in 200 ml of deionized water and stirred for 5 hours at 95° C. It is allowed to cool, filtered with a 2 $\mu$ filter, and the title product is isolated from the filtrate by freeze-drying as a colorless, amorphous powder.

Yield: 11.30 g (quantitative), water content: 7.3%; Elementary analysis (relative to anhydrous substance): Cld: C, 51.09/H, 5.46/N, 5.42/Ca, 5.17/P, 3.99. Fnd: C, 51.21/H, 5.55/N, 5.53/Ca, 5.08/P, 4.10.

EXAMPLE 7

Calcium (4-),[[(4R)-4-[bis[(carboxy-.kappa.O) methyl]amino-.kappa.N]-6,9-bis[(carboxy-.kappa.O) methyl]-1-[(4,4-diphenylcyclohexyl)oxy]-1-hydroxy-2-oxa-6,9-diaza-1-phosphaundecan-11-ylic-acid-.kappa.N5,.kappa.N9,.kappa.011]1-oxidato (6-)]-, Tetrahydrogen 10 g (12.88 mmol) of MS-325 and 0.954 g (12.88 mmol) of calcium hydroxide are added to 100 ml of water, and 1.55 g (38.64 mmol) of sodium hydroxide is added. It is heated for 5 hours at 80° C. It is cooled to 10° C. and set at pH 2.5 with 10% aqueous hydrochloric acid. Then, 200 ml of isopropanol is added, and it is cooled to 0° C. It is precipitated for 3 hours at 0° C., and then it is filtered off from deposited precipitate. The precipitate that is filtered off is washed twice with 50 ml of ethanol and twice with 100 ml of diethyl ether and dried in a vacuum.

Yield: 8.76 g (87% of theory) of a colorless, crystalline powder. Water content: 7.6% elementary analysis (relative to anhydrous substance): Cld:/C, 51.09/H, 5.46/N, 5.42/Ca, 5.17/P, 3.99. Fnd:/C, 50.87/H, 5.64/N, 5.28/Ca, 5.01/P, 3.72.

EXAMPLE 8

Calcium(4-),[[(4R)-4-[bis[(carboxy-.kappa.O) methyl]amino-.kappa.N]-6,9-bis[(carboxy-.kappa.O) methyl]-1-[(4,4-diphenylcyclohexyl)oxy]-1-hydroxy-2-oxa-6,9-diaza-1-phosphaundecan-11-ylic-acid-.kappa.N6,.kappa.N9,.kappa.011]1-oxidato (6-)]-, Disodium, Dihydrogen 10.0 g (12.88 mmol/95% content (according to weight)) of MS-325 ligand, 1.288 g (12.88 mmol) of calcium carbonate and 1.03 g (25.76 mmol) of sodium hydroxide are dissolved in 200 ml of deionized water and stirred for 5 hours at 95° C. It is allowed to cool, filtered with a 2 $\mu$ filter, and the title product is isolated from the filtrate by freeze-drying as a colorless, amorphous powder.

Yield: 11.70 g (quantitative), water content: 9.8%; Elementary analysis (relative to anhydrous substance): Cld: C, 48.35/H, 4.92/N, 5.13/Ca, 4.89/Na, 5.61/P, 3.78. Fnd: C, 48.49/H, 5.01/N, 5.24/Ca, 5.00/Na, 5.50/P, 3.90.

EXAMPLE 9

Calcium(4-),[[(4R)-4-[bis[(carboxy-.kappa.O)
methyl]amino-.kappa.N]-6,9-bis[(carboxy-.kappa.O)
methyl]-1-[(4,4-diphenylcyclohexyl)oxy]-1-
hydroxy-2-oxa-6,9-diaza-1-phosphaundecan-11-ylic-
acid-.kappa.N6,.kappa.N9,.kappa.011]1-oxidato
(6-)]-, Trisodium, Monohydrogen 10.0 g (12.88 mmol/95% content (according to weight)) of MS-325 ligand, 0.954 g (12.88 mmol) of calcium hydroxide and 1.546 g (38.64 mmol) of sodium hydroxide are dissolved in 200 ml of deionized water and stirred for 5 hours at 95° C. It is allowed to cool, filtered with a 2 µ filter, and the title product is isolated from the filtrate by freeze-drying as a colorless, amorphous powder.

Yield: 12.14 g (quantitative), water content: 10.7%; Elementary analysis (relative to anhydrous substance): Cld: C, 47.09/H, 4.67/N, 4.99/Ca, 4.76/Na, 8.19/P, 3.68. Fnd: C, 47.22/H, 4.78/N, 5.12/Ca, 4.70/Na, 8.27/P, 3.80.

EXAMPLE 10

Calcium(4-),[[(4R)-4-[bis[(carboxy-.kappa.O)
methyl]amino-.kappa.N]-6,9-bis[(carboxy-.kappa.O)
methyl]-1-[(4,4-diphenylcyclohexyl)oxy]-1-
hydroxy-2-oxa-6,9-diaza-1-phosphaundecan-11-ylic-
acid-.kappa.N6,.kappa.N9,.kappa.011]1-oxidato
(6-)]-, Dimeglumine, Dihydrogen 10.0 g (12.88 mmol/95% content (according to weight)) of MS-325 ligand, 0.954 g (12.88 mmol) of calcium hydroxide and 5.03 g (25.76 mmol) of meglumine are dissolved in 200 ml of deionized water and stirred for 5 hours at 95° C. It is allowed to cool, filtered with a 2 µ filter, and the title product is isolated from the filtrate by freeze-drying as a colorless, amorphous powder.

Yield: 17.22 g (quantitative), water content: 12.8%; Elementary analysis (relative to anhydrous substance): Cld: C, 48.41/H, 6.57/N, 6.01/Ca, 3.44/P, 2.66. Fnd: C, 48.28/H, 6.69/N, 6.12/Ca, 3.52/P, 2.77.

EXAMPLE 11

Calcium(4-),[[(4R)-4-[bis[(carboxy-.kappa.O)
methyl]amino-.kappa.N]-6,9-bis[(carboxy-.kappa.O)
methyl]-1-[(4,4-diphenylcyclohexyl)oxy]-1-
hydroxy-2-oxa-6,9-diaza-1-phosphaundecan-11-ylic-
acid-.kappa.N6,.kappa.N9,.kappa.011]1-oxidato
(6-)]-, Trimeglumine, Monohydrogen 10.0 g (12.88 mmol/95% content (according to weight)) of MS-325 ligand, 1.288 g (12.88 mmol) of calcium carbonate and 7.54 g (38.64 mmol) of meglumine are dissolved in 200 ml of deionized water and stirred for 5 hours at 95° C. It is allowed to cool, filtered with a 2 µ filter, and the title product is isolated from the filtrate by freeze-drying as a colorless, amorphous powder.

Yield: 19.70 g (quantitative), water content: 11.0%; Elementary analysis (relative to anhydrous substance): Cld: C, 47.64/H, 6.89/N, 6.17/Ca, 2.94/P, 2.28. Fnd: C, 47.80/H, 6.97/N, 6.28/Ca, 3.00/P, 2.40.

EXAMPLE 12

Calcium(4-),[[(4R)-4-[bis-[(carboxy-.kappa.O)
methyl]amino-.kappa.N]-6,9-bis[(carboxy-.kappa.O)
methyl]-1-[(4,4-diphenylcyclohexyl)oxy]-1-
hydroxy-2-oxa-6,9-diaza-1-phosphaundecan-11-ylic-
acid-.kappa.N6,.kappa.N9,.kappa.011]1-oxidato
(6-)]-, sodium 3.5, Hydrogen 0.5

10.0 g (12.88 mmol/95% content (according to weight) of MS-325 ligand, 1.288 g (12.88 mmol) of calcium carbonate and 1.546 g of 38.84 mmol) of sodium hydroxide are dissolved in 200 ml of deionized water and stirred for 5 hours at 95° C. It is allowed to cool and set at pH 7.4 by adding a 5% aqueous solution of sodium hydroxide. It is filtered, and the title compound is isolated by freeze-drying.

Yield: 12.01 g (quantitative) of a colorless powder, water content: 8.6%; Elementary analysis (relative to anhydrous substance) calculated as 3.5 sodium salt; Cld: C, 46.68/H, 4.55/N, 4.93/Ca, 4.70/Na, 9.44/P, 3.63. Fnd. C, 46.61/H, 4.43/N, 5.02/Ca, 4.81/Na, 9.51/P, 3.71.

EXAMPLE 13

Calcium(4-),[[(4R)-4-[bis[(carboxy-.kappa.O)
methyl]amino-.kappa.N]-6,9-bis[(carboxy-.kappa.O)
methyl]-1-[(4,4-diphenylcyclohexyl)oxy]-1-
hydroxy-2-oxa-6,9-diaza-1-phosphaundecan-11-ylic-
acid-.kappa.N6,.kappa.N9,.kappa.011]1-oxidato
(6-)]-, Meglumine 3.5, Hydrogen 0.5

10.0 g (12.88 mmol/95% content (according to weight) of MS-325 ligand, 1.288 g (12.88 mmol) of calcium carbonate and 7.54 g (38.64 mmol) of meglumine are dissolved in 200 ml of deionized water and stirred for 5 hours at 95° C. It is allowed to cool and set at pH 7.4 by adding a 5% aqueous solution of meglumine. It is filtered, and the title compound is isolated by freeze-drying.

Yield: 20.82 g (quantitative) of a colorless powder, water content: 9.7%; Elementary analysis (relative to anhydrous substance) calculated as 3.5 meglumine salt; Cld: C, 47.32/H, 7.04/N, 6.24/Ca, 2.75/P, 2.12. Fnd: C, 47.48/H, 7.15/N, 6.36/Ca, 2.87/P 2.17.

EXAMPLE 14

Production of a Formulation of the Gadolinium
Complex of MS-325 as Sodium Salt (200 mmol)
(5% Excess Complexing Agent of the Title
Compound of Example 1)

18.12 g (50 mmol) of gadolinium oxide, 77.65 (100 mmol/95% content (according to weight) of MS-325, 4.318 g (5.0 mmol) of the title compound of Example 1, and 11.2 g (280 mmol) of sodium hydroxide are stirred in 350 ml of tris-HCl buffer (10 mmol/l) at pH 7.4 for 6 hours at 95° C. It is allowed to cool to room temperature and set at pH 7.4 with 20% aqueous sodium hydroxide. Then, it is made up with tris-HCl buffer (10 mmol/l/ph 7.4 to a total volume of 500 ml, the solution is filtered with a 2 µ filter, and the filtrate is decanted into vials.

EXAMPLE 15

Production of a Formulation of the Gadolinium
Complex of MS-325 as Meglumine Salt (200
mmol) (5% Excess Complexing Agent of the Title
Compound of Example 4)

18.12 g (50 mmol) of gadolinium oxide, 77.65 (100 mmol/95% content (according to weight) of MS-325, 7.783 g (5.0 mol) of the title compound of Example 4 and 54.66 g (280 mmol) of meglumine are stirred in 350 ml of tris-HCl buffer (10 mmol/l) at pH 7.4 for 6 hours at 95° C. It is allowed to cool to room temperature, and the pH is set at 7.4 with 20% aqueous meglumine. Then, it is made up with tris-HCl buffer (10 mmol/l/pH 7.4) to a total volume of 500 ml, the solution is filtered with a 2 µ filter, and the filtrate is decanted into vials.

EXAMPLE 16

Production of a Formulation of the Gadolinium
Complex of MS-325 as Sodium Salt (200 mmol)
(5% Excess Complexing Agent of the Title
Compound of Example 7)

18.12 g (50 mmol) of gadolinium oxide, 77.65 (100 mmol/95% content (according to weight) of MS-325, 3.879 g (5.0 mmol) of the title compound of Example 7 and 11.2 g (280 mmol) of sodium hydroxide are stirred in 350 ml of tris-HCl buffer (10 mmol/l, pH 7.4) for 6 hours at 95° C. It is allowed to cool to room temperature and set at pH 7.4 with 20% aqueous sodium hydroxide. Then, it is made up with tris-HCl buffer (10 mmol/l/pH 7.4) to a total volume of 500 ml, the solution is filtered with a 2 $\mu$ filter, and the filtrate is decanted into vials.

EXAMPLE 17

Production of a Formulation of the Gadolinium Complex of MS-325 as Sodium Salt (200 mmol) (5% Excess Complexing Agent of the Title Compound of Example 8)

18.12 g (50 mmol) of gadolinium oxide, 77.65 (100 mmol/95% content (according to weight) of MS-325, 4.099 g (5.0 mmol) of the title compound of Example 8 and 11.2 g (280 mmol) of sodium hydroxide are stirred in 350 ml of tris-HCl buffer (10 mmol/l, pH 7.4) for 6 hours at 95° C. It is allowed to cool to room temperature and set at pH 7.4 with 20% aqueous sodium hydroxide. Then, it is made up with tris-HCl buffer (10 mmol/l/pH 7.4) to a total volume of 500 ml, the solution is filtered with a 2 $\mu$ filter, and the filtrate is decanted into vials.

EXAMPLE 18

Production of a Formulation of the Gadolinium Complex of MS-325 as Sodium Salt (200 mmol) (5% Excess Complexing Agent of the Title Compound of Example 9)

18.12 g (50 mmol) of gadolinium oxide, 77.65 (100 mmol/95% content (according to weight) of MS-325, 4.209 g (5.0 mmol) of the title compound of Example 9 and 11.2 g (280 mmol) of sodium hydroxide are stirred in 350 ml of tris-HCl buffer (10 mmol/l, pH 7.4) for 6 hours at 95° C. It is allowed to cool to room temperature and set at pH 7.4 with 20% aqueous sodium hydroxide. Then, it is made up with tris-HCl buffer (10 mmol/l/pH 7.4) to a total volume of 500 ml, the solution is filtered with a 2 $\mu$ filter, and the filtrate is decanted into vials.

EXAMPLE 19

Production of a Formulation of the Gadolinium Complex of MS-325 as a Sodium Salt (200 mmol) (5% Excess Complexing Agent of the Title Compound of Example 12)

18.12 g (50 mmol) of gadolinium oxide, 77.65 (100 mmol/95% content (real weight) of MS-325, 4.26 g (5.0 mmol) of the title compound of Example 12 and 11.2 g (280 mmol) of sodium hydroxide are stirred in 350 ml of tris-HCl buffer (10 mmol/l, pH 7.4) for 6 hours at 95° C. It is allowed to cool to room temperature and set at pH 7.4 with 20% aqueous sodium hydroxide. Then, it is made up with tris-HCl buffer (10 mmol/l/pH 7.4) to a total volume of 500 ml, the solution is filtered with a 2 $\mu$ filter, and the filtrate is decanted into vials.

EXAMPLE 20

Production of a Formulation of the Gadolinium Complex of MS-325 as Meglumine Salt (200 mmol) (5% Excess Complexing Agent of the Title Compound of Example 13)

18.12 g (50 mmol) of gadolinium oxide, 77.65 (100 mmol/95% content (according to weight) of MS-325, 7.297 g (5.0 mmol) of the title compound of Example 13 and 54.66 g (280 mmol) of meglumine are stirred in 350 ml of tris-HCl buffer (10 mmol/l) at pH 7.4 for 6 hours at 95° C. It is allowed to cool to room temperature and set at pH 7.4 with 20% aqueous meglumine. Then, it is made up with tris-HCl buffer (10 mmol/l/pH 7.4) to a total volume of 500 ml, the solution is filtered with a 2 $\mu$ filter, and the filtrate is decanted into vials.

EXAMPLE 21

Production of a Formulation of the Gadolinium Complex of MS-325 as Meglumine Salt (200 mmol) (5% Excess Complexing Agent of the Title Compound of Example 10)

18.12 g (50 mmol) of gadolinium oxide, 77.65 (100 mmol/95% content (according to weight) of MS-325, 5.83 g (5.0 mmol) of the title compound of Example 10 and 54.66 g (280 mmol) of meglumine are stirred in 350 ml of tris-HCl buffer (10 mmol/l) at pH 7.4 for 6 hours at 95° C. It is allowed to cool to room temperature and set at pH 7.4 with 20% aqueous meglumine. Then, it is made up with tris-HCl buffer (10 mmol/l/pH 7.4) to a total volume of 500 ml, the solution is filtered with a 2 $\mu$ filter, and the filtrate is decanted into vials.

EXAMPLE 22

Production of a Formulation of the Gadolinium Complex of MS-325 as Sodium Salt (200 mmol) (5% Excess Complexing Agent of the Title Compound of Example 1)

18.12 g (50 mmol) of gadolinium oxide, 77.65 (100 mmol/95% content (according to weight) of MS-325, 1.08 g (1.25 mmol) of the title compound of Example 1, and 11.2 g (280 mmol) of sodium hydroxide are stirred in 350 ml of tris-HCl buffer (10 mmol/l, pH 7.4) for 6 hours at 95° C. It is allowed to cool to room temperature and set at pH 7.4 with 20% aqueous sodium hydroxide. Then, it is made up with tris-HCl buffer (10 mmol/l/pH 7.4) to a total volume of 500 ml, the solution is filtered with a 2 $\mu$ filter, and the filtrate is decanted into vials.

EXAMPLE 23

Production of a Formulation of the Gadolinium Complex of MS-325 as Sodium Salt (200 mmol) (2.5% Excess Complexing Agent of the Title Compound of Example 1)

18.12 g (50 mmol) of gadolinium oxide, 77.65 (100 mmol/95% content (according to weight) of MS-325, 2.16 g (2.50 mmol) of the title compound of Example 1, and 11.2 g (280 mmol) of sodium hydroxide are stirred in 350 ml of tris-HCl buffer (10 mmol/l, pH 7.4) for 6 hours at 95° C. It is allowed to cool to room temperature and set at pH 7.4 with 20% aqueous sodium hydroxide. Then, it is made up with tris-HCl buffer (10 mmol/l/pH 7.4) to a total volume of 500 ml, the solution is filtered with a 2 $\mu$ filter, and the filtrate is decanted into vials.

EXAMPLE 24

Production of a Formulation of the Gadolinium Complex of MS-325 as Meglumine Salt (200 mmol) (1.25% Excess Complexing Agent of the Title Compound of Example 4)

18.12 g (50 mmol) of gadolinium oxide, 77.65 (100 mmol/95% content (according to weight) of MS-325, 1.946 g (1.25 mmol) of the title compound of Example 4 and 54.66 g (280 mmol) of meglumine are stirred in 350 ml of tris-HCl buffer (10 mmol/l) at pH 7.4 for 6 hours at 95° C. It is allowed to cool to room temperature and set at pH 7.4 with 20% aqueous meglumine. Then, it is made up with tris-HCl buffer (10 mmol/l/pH 7.4) to a total volume of 500 ml, the solution is filtered with a 2 μ filter, and the filtrate is decanted into vials.

EXAMPLE 25

Production of a Formulation of the Gadolinium Complex of MS-325 as Meglumine Salt (200 mmol) (2.5% Excess Complexing Agent of the Title Compound of Example 4)

18.12 g (50 mmol) of gadolinium oxide, 77.65 (100 mmol/95% content (according to weight) of MS-325, 3.891 g (2.5 mmol) of the title compound of Example 4 and 54.66 g (280 mmol) of meglumine are stirred in 350 ml of tris-HCl buffer (10 mmol/l/pH 7.4) for 6 hours at 95° C. It is allowed to cool to room temperature and set at pH 7.4 with 20% aqueous meglumine. Then, it is made up with tris-HCl buffer (10 mmol/l/pH 7.4) to a total volume of 500 ml, the solution is filtered with a 2 μ filter, and the filtrate is decanted into vials.

EXAMPLE 26

Production of a Formulation of the Gadolinium Complex of MS-325 as Sodium Salt (200 mmol) (5% Excess Complexing Agent of the Title Compound of Example 1)

Alternative Process 18.12 g (50 mmol) of gadolinium oxide, 77.65 (100 mmol/95% content (according to weight) of MS-325, and 11.2 g (280 mmol) of sodium hydroxide are stirred in 350 ml of tris-HCl buffer (10 mmol/l, pH 7.4) for 6 hours at 95° C. It is allowed to cool to room temperature, 4.318 g (5.0 mmol) of the title compound of Example 1 is added, and it is set at pH 7.4 with 20% aqueous sodium hydroxide. Then, it is made up with tris-HCl buffer (10 mmol/l, pH 7.4) to a total volume of 500 ml, the solution is filtered with a 2 μ filter, and the filtrate is decanted into vials.

EXAMPLE 27

Production of a Formulation of the Gadolinium Complex of MS-325 as Meglumine Salt (200 mmol) (5% Excess Complexing Agent of the Title Compound of Example 4)

Alternative Process 18.12 g (50 mmol) of gadolinium oxide, 77.65 (100 mmol/95% content (according to weight) of MS-325, and 54.66 g (280 mmol) of meglumine are stirred in 350 ml of tris-HCl buffer (10 mmol/l, pH 7.4) for 6 hours at 95° C. It is allowed to cool to room temperature, 7.783 g (5.0 mmol) of the title compound of Example 4 is added, and it is set at pH 7.4 with 20% aqueous meglumine. Then, it is made up with tris-HCl buffer (10 mmol/l, pH 7.4) to a total volume of 500 ml, the solution is filtered with a 2 μ filter, and the filtrate is decanted into vials.

EXAMPLE 28

Production of a Formulation of the Gadolinium Complex of MS-325 as Sodium Salt (200 mmol) (2.50% Excess Complexing Agent of the Title Compound of Example 1)

Alternative Process 18.12 g (50 mmol) of gadolinium oxide, 77.65 (100 mmol/95% content (according to weight) of MS-325, and 11.2 g (280 mmol) of sodium hydroxide are stirred in 350 ml of tris-HCl buffer (10 mmol/l, pH 7.4) for 6 hours at 95° C. It is allowed to cool to room temperature, 2.16 g (2.50 mmol) of the title compound of Example 1 is added, and it is set at pH 7.4 with 20% aqueous sodium hydroxide. Then, it is made up with tris-HCl buffer (10 mmol/l, pH 7.4) to a total volume of 500 ml, the solution is filtered with a 2 p filter, and the filtrate is decanted into vials.

EXAMPLE 29

Production of a formulation of the Gadolinium Complex of MS-325 as Meglumine Salt (200 mmol) (2.50% Excess Complexing Agent of the Title Compound of Example 4)

Alternative Process 18.12 g (50 mmol) of gadolinium oxide, 77.65 (100 mmol/95% content (according to weight) of MS-325, and 54.66 9 (280 mmol) of meglumine are stirred in 350 ml of tris-HCl buffer (10 mmol/l, pH 7.4) for 6 hours at 95° C. It is allowed to cool to room temperature, 3.891 g (2.50 mmol) of the title compound of Example 4 is added, and it is set at pH 7.4 with 20% aqueous meglumine. Then, it is made up with tris-HCl buffer (10 mmol/l, pH 7.4) to a total volume of 500 ml, the solution is filtered with a 2 μ filter, and the filtrate is decanted into vials.

EXAMPLE 30

$^1$H and $^{31}$P NMR Spectra of the Compounds of Examples 1 and 2

All measurements were carried out on an AMX 400 NMR-spectrometer (400 MHz, Bruker). $^1$H chemical shifts are indicated in δ (ppm) relative to the solvent (D$_2$O δ=4.8 ppm). $^{31}$P chemical shifts are indicated in δ (ppm) relative to the external standard H$_3$PO$_4$ (85%, δ=0 ppm).

Title compounds of Examples 1 and 2 were dissolved in D$_2$O, and the spectrum was taken up at room temperature. Result:

Title Compound of Example 1

$^1$H: 1.4–1.7 (m, 2H), 1.8–2.1 (m, 3H), 2.15–2.25 (m, 2H), 2.32 (t, 12 Hz, 1H), 2.5–2.92 (m, 7H), 2.95–3.4 (m, 8H), 3.45 (d, 16 Hz, 1H), 3.66 (d, 16 Hz, 1H), 3.8–3.95 (m, 2H), 4.23 (m, 1H), 7.15–7.25 (m, 2H), 7.25–7.5 (m, 8H); $^{31}$P: 0.38 (q, 6 Hz), 0.51 (q, 6 Hz).

Title Compound of Example 2

$^1$H: 1.20–1.45 (broad, 2H), 1.5–1.7 (broad, 2H), 1.75–2.05 (m, 3H), 2.1–2.5 (m, 6H), 2.65–3.20 (m, 8H), 3.24 (d, 16 Hz, b 1H), 3.45 (d, 16 Hz, 1H), 3.50–3.80 (m, 4H), 4.02 (m, 1H), 6.75–7.20 (m, 10H); $^{31}$P: 0.25 (q, 6 Hz), 0.10 (q, 5 Hz).

The preceding examples can be repeated with similar success by substituting the generically or specifically described reactants and/or operating conditions of this invention for those used in the preceding examples.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

The entire disclosure of all applications, patents and publications, cited above and below, and of corresponding U.S. application Ser. No. 09/396,965, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A calcium complex of [[(4R)-4-[bis[(carboxy-.kappa.O)methyl]amino-.kappa.N]-6,9-bis[(carboxy-.kappa.O)methyl]-1-[(4,4-diphenylcyclohexyl)oxyl]-1-hydroxy-2-oxa-6,9-diaza-1-phosphaundecan-11-ylic-acid-.kappa.N6,.kappa.N9,.kappa.O11]1-oxidata(6-)]-hexahydrogen (MS-325), or a salt thereof with a one or more physiologically compatible cations, in each case essentially free of chelates of imaging metals and MS-325.

* * * * *